US012018135B2

(12) United States Patent
Scher et al.

(10) Patent No.: US 12,018,135 B2
(45) Date of Patent: Jun. 25, 2024

(54) ENCAPSULATION BY CROSS-LINKING OF ANIONIC POLYMERS BY pH INDUCED DISSOCIATION OF CATION-CHELATE COMPLEXES

(71) Applicant: THE REGENTS OF THE UNIVERSITY OF CALIFORNIA, Oakland, CA (US)

(72) Inventors: Herbert B. Scher, Moraga, CA (US); Scott Strobel, Davis, CA (US); Tina Jeoh Zicari, Davis, CA (US); Dana Wong, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 506 days.

(21) Appl. No.: 17/336,766

(22) Filed: Jun. 2, 2021

(65) Prior Publication Data
US 2022/0025132 A1 Jan. 27, 2022

Related U.S. Application Data

(63) Continuation of application No. PCT/US2019/064333, filed on Dec. 3, 2019.
(Continued)

(51) Int. Cl.
C08J 3/24 (2006.01)
B01J 13/04 (2006.01)
(Continued)

(52) U.S. Cl.
CPC .............. C08J 3/24 (2013.01); B01J 13/043 (2013.01); B01J 13/14 (2013.01); C08K 3/16 (2013.01);
(Continued)

(58) Field of Classification Search
CPC ................. B01J 13/043; B01J 13/14
See application file for complete search history.

(56) References Cited

U.S. PATENT DOCUMENTS 4,350,804 A 9/1982 Ostrowski
6,497,902 B1 * 12/2002 Ma .................. A61K 9/0019
424/78.18
(Continued)

FOREIGN PATENT DOCUMENTS

PH 12007000169 B 4/2009
WO 2020117873 A1 6/2020

OTHER PUBLICATIONS

ISA/US, United States Patent and Trademark Office, International Search Report and Written Opinion dated Feb. 7, 2020, related PCT international application No. PCT/US2019/064333, pp. 1-11, claims searched, pp. 12-17.

Primary Examiner — Mary Lynn F Theisen
(74) Attorney, Agent, or Firm — O'BANION & RITCHEY LLP; John P. O'Banion

(57) ABSTRACT

Microencapsulation methods are provided using encapsulant, fiber or film forming compositions of a cross-linkable anionic polymer, a multivalent cation salt, a chelating agent, and a volatile base. During the formation of this composition, the generally acidic chelating agent is titrated with a volatile base to an elevated pH to improve ion-binding capability. Multivalent cations are sequestered in cation-chelate complexes. Cross-linkable polymers in this solution will remain freely dissolved until some disruption of equilibrium induces the release of the free multivalent cations from the cation-chelate complex. Vaporization of the volatile base drops the pH of the solution causing the cation-chelate complexes to dissociate and liberate multivalent cations that associate with the anionic polymer to form a cross-linked matrix. During spray-drying, the formation of a
(Continued)

wet particle, polymer cross-linking, and particle drying occur nearly simultaneously.

12 Claims, 4 Drawing Sheets

Related U.S. Application Data

(60) Provisional application No. 62/775,331, filed on Dec. 4, 2018.

(51) Int. Cl.
| | | |
|---|---|---|
| *B01J 13/14* | (2006.01) | |
| *C08K 3/16* | (2006.01) | |
| *C08K 3/28* | (2006.01) | |
| *C08K 5/095* | (2006.01) | |
| *C08K 5/5357* | (2006.01) | |

(52) U.S. Cl.
CPC ............... *C08K 3/28* (2013.01); *C08K 5/095* (2013.01); *C08K 5/5357* (2013.01); *C08J 2305/04* (2013.01); *C08J 2305/08* (2013.01); *C08K 2003/162* (2013.01)

(56) References Cited

U.S. PATENT DOCUMENTS

| | | | |
|---|---|---|---|
| 2009/0053317 A1 | 2/2009 | Vigo | |
| 2011/0098363 A1 | 4/2011 | Garnier | |
| 2017/0333360 A1 | 11/2017 | Zicari | |
| 2019/0284349 A1* | 9/2019 | Bassett | .................... C08K 3/08 |
| 2021/0307320 A1* | 10/2021 | Allen | .................... B01J 13/046 |

* cited by examiner

```
100
 ↓
110 — Combine chelating agent,
      volitile base and cargo
         ↓
120 — Add multivalent cation
      cross-linking agent
         ↓
130 — Add an anionic polymer
         ↓
140 — Atomize and heat the formulation
         ↓
150 — Volatilize base to release
      multivalent cations from
      chelating agent
         ↓
160 — Cross-link polymer with free
      cations to microcapsulate cargo
```

- 210 — Combine chelating polymer, volatile base and cargo
- 220 — Add multivalent cation cross-linking agent
- 230 — Atomize and heat the formulation
- 240 — Volatilize base to release multivalent cations from chelating polymer
- 250 — Cross-link polymer with free cations to microcapsulate cargo

FIG. 3

ENCAPSULATION BY CROSS-LINKING OF ANIONIC POLYMERS BY pH INDUCED DISSOCIATION OF CATION-CHELATE COMPLEXES

CROSS-REFERENCE TO RELATED APPLICATIONS

This application claims priority to, and is a 35 U.S.C. § 111(a) continuation of, PCT international application number PCT/US2019/064333 filed on Dec. 3, 2019, incorporated herein by reference in its entirety, which claims priority to, and the benefit of, U.S. provisional patent application Ser. No. 62/775,331 filed on Dec. 4, 2018, incorporated herein by reference in its entirety. Priority is claimed to each of the foregoing applications.

The above-referenced PCT international application was published as PCT International Publication No. WO 2020/117873 A1 on Jun. 11, 2020, which publication is incorporated herein by reference in its entirety.

STATEMENT REGARDING FEDERALLY SPONSORED RESEARCH OR DEVELOPMENT

This invention was made with Government support under Grant No. 2014-67017-21641 awarded by the United States Department of Agriculture (USDA AFRI). The Government has certain rights in the invention.

INCORPORATION-BY-REFERENCE OF COMPUTER PROGRAM APPENDIX

Not Applicable

BACKGROUND

1. Technical Field

The technology of this disclosure pertains generally to film and fiber formation and encapsulation methods, and more particularly to methods for producing microcapsules in a single step by cross-linking anionic polymers through pH-induced dissociation of cation-chelate complexes with the volatilization of a volatile base. The reduction in pH with volatilization of the base releases' multivalent ions from the ion-chelate complexes initiating cross-linking of the available polymers forming a film, fiber or capsule.

2. Background Discussion

Microencapsulation of biomolecules, cells and chemicals is often used in the food and pharmaceutical industries to increase the stability and shelf life of the encapsulated material and to control the delivery and context of material release. Generally, the capsule matrix provides a protective layer against environmental conditions that could damage the encapsulated material and can regulate the release of the encapsulated compounds at a target location. Encapsulation can also be used to package and store almost any kind of microscopic particles or droplets in a capsule shell. Many different types of materials that are used for both therapeutic and non-therapeutic applications can be encapsulated in microcapsules.

Release of the material from the capsules can be accomplished through diffusion, by mechanical rupture, or by chemical or electrical disintegration of the capsule wall. The conditions of the ultimate target environment of the capsules will normally influence the nature of the capsules that are created.

For example, the size of the microcapsules can be an important factor in the effective movement of the capsules across cell membranes as well as mediating the inflammatory or immune response that is made by the cell to the microcapsules. There are many other uses for microcapsules that are smaller than the 300 μm limits of traditional spray drying methods in a wide variety of applications.

Many conventional encapsulation methods use polymers as an encapsulation matrix to form capsules by chemically cross-linking the polymer molecules. One group of conventional encapsulation approaches involves interfacial polymerization where the capsule shell is formed at or near the interface between continuous and discontinuous phases. Condensation or addition polymerization reactions between monomers in each phase are common approaches.

Another approach in the art is to form droplets of polymer and cargo and the capsule is cross-linked upon contact with a solution containing cross-linking agents. For example, alginates have been used for encapsulation for many years. Alginates are an appealing encapsulation matrix because of their biodegradability and biocompatibility and low cost. The traditional encapsulation process for alginates involves dissolving or dispersing the cargo in a sodium alginate solution and forming droplets of solution that are then cross-linked by contact with a calcium chloride solution.

However, this procedure is difficult to scale-up and produces undesirably large alginate beads. Although spray drying methods can form stable micron-scale particles, achieving cross-linked alginate particles by spray-drying has historically not been practical due to rapid gelation prior to spraying.

The direct mixing of alginate and calcium chloride solutions or similar materials also fails to produce homogeneous gels because of the very rapid binding kinetics of the ions. This also produces beads or capsules with the highest cross-linked alginate concentrations at the outer surface of the capsule with a decreasing gradient of cross-linking towards the center of the gel. Conventional internal gelation/emulsification methods (e.g. emulsify alginate and insoluble calcium in oil, add acid to reduce pH and then crosslink) require numerous processing steps (including emulsification, gelation, separation from oil, washing, drying).

Advances were made to improve the alginate droplet—calcium chloride bath process by utilizing a formulation of an acid neutralized with a volatile base, a salt of a multivalent cation which is insoluble under basic conditions and a polymer such as sodium alginate that can cross link in the presence of multivalent cations. When this formulation is atomized into droplets in a spray dryer, crosslinking is achieved when the volatile base is vaporized resulting in a reduction in pH and the release of multivalent cations from the acid soluble salt. The free multivalent cations can then cross link the polymer forming an encapsulating matrix.

Accordingly, there is a need for a spray drying process that can successfully encapsulate a wide variety of cargo materials that is not limited in particle size and has controllable cross-linking conditions.

BRIEF SUMMARY

The present technology generally provides methods for the production of microcapsules prepared with a single cross-linking step via spray drying as well as methods of polymer film and fiber formation. Although the formation of microcapsules by spray drying is used to illustrate the process, the process mechanism can be adapted to electrospinning and the formation of fibers, particles or films.

Effective spray-drying relies on pumping a low-viscosity solution through an atomizer which has historically precluded the ability to form ion-mediated cross-linking by spray drying. Therefore, the methods are particularly useful for spray-drying applications where premature cross-linking of the polymers prevents effective atomization of the spray solution. The methods also provide control over the capsule cargo release characteristics controlling cross-linking and hydration properties of the encapsulation as well as the capsule size and size distribution.

Encapsulation polymer cross-linking is controlled by using a chelating agent-cation complex and a volatile base to control ion availability. Ion mediated cross-linking of the polymer molecules is initially prevented by pH control with the volatile base. The change in pH by the vaporization of the volatile base triggers the release of multivalent ions in the atomized droplet, fiber or film that were originally sequestered by the chelating agent-cation complex. Therefore, the timing of the cross-linking can be controlled by the timing of the volatilization of the base, which lowers the pH and releases the ions from the complex to spontaneously form cross-links between the polymer molecules. In one preferred method, cross-linking of the polymer is achieved by internal gelation that takes place during spray drying, encapsulating the cargo in a microcapsule.

In the illustrated spray-drying application, the preferred spray formulation includes cargo, one or more types of polymer molecules, a chelating agent-cation complex, and at least one volatile base. In one embodiment, the formulation is made by combining an aqueous solution of the polymer, cargo, multivalent ion source and chelating agent with a volatile base at a pH that is sufficiently high such that the cations are completely chelated in solution by forming chelating agent-cation complexes.

The formulation can be atomized, and the droplets directed into an evaporation chamber where drying takes place. As the droplets dry through evaporation of the water or solvent, the volatile base in the formulation volatilizes, causing a drop in pH and the protons outcompete the cation in the chelator-cation complex.

Optionally, a weak acid may be included in the formulation to provide additional pH control. This results in the release of cations into the droplet solution resulting in the crosslinking of the polymers to form a cross-linked matrix encapsulating the cargo. Particles collected at the outlet of the evaporation chamber are dried, cross-linked microcapsules containing the cargo. The methods may be particularly useful for spray-drying applications where premature cross-linking of the polymers in the feed solution prevents effective atomization of the product.

Accordingly, the present technology utilizes a different mechanism and is an improvement over the mechanism of in situ solubilization of a multivalent cation salt to produce free multivalent cations resulting in crosslinking of the polymer. In contrast, the process described here releases multivalent cations in situ as a chelating agent is protonated and loses its ability to complex with the multivalent cations. The free multivalent cations can then cross-link the polymer.

One improvement of this mechanism includes the elimination of the base insoluble multivalent cation salt so that the spray dry feed is a solution of multivalent cation-chelate complex as opposed to a dispersion of a base insoluble multivalent cation salt. The spray solution described herein includes the formation of a multivalent cation—chelate complex that is less viscous than the base insoluble multivalent cation salt dispersion and hence it is easier to atomize and there is no residual insoluble multivalent cation salt in the spray dry product. In addition, in most cases, the chelate agent mediated process does not require an additional acid (such as succinic acid) as the chelate agent also serves as the acid.

According to one aspect of the technology, a method with a one-step process is provided that includes almost simultaneous wet particle formation, polymer cross-linking and particle drying.

Another aspect of the technology is to provide a method for controlling the timing of cation-mediated cross-linking of polymers such as alginates, soy or whey proteins and any anionic polymers to enable spray-dry encapsulation of biological moieties and other sensitive cargo.

Yet another aspect of the technology is to provide a microencapsulation method that can be adapted for use with many different types of biocompatible polymers such as alginate, carboxymethyl cellulose, hyaluronic acid, carrageenan, soy protein, whey protein, and pectins.

According to another aspect of the technology, a method is provided that can control the release rate of the encapsulated active ingredient by controlling the degree of cross-linking with 1) the choice of chelating agent; 2) the concentration of cation salt relative to chelating agent concentration; 3) choice of polymer, and 4) processing conditions.

A further aspect of the technology is to provide a method that can be modulated to control the microcapsule structural characteristics and produce capsules of consistent sizes that is easy to use and inexpensive to produce.

Another aspect of the technology is to provide a method that can be used in multiple industries employing spray-drying to encapsulate active agents such as encapsulating biological molecules, cells, probiotics, nutraceuticals and other organic or inorganic chemicals.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 2 is a functional block diagram of a method for fabricating microcapsules according to another embodiment of the technology.

FIG. 3 is a functional block diagram of a method for fabricating microcapsules with chelating polymers according to another embodiment of the technology.

DETAILED DESCRIPTION

Referring more specifically to the drawings, for illustrative purposes several embodiments of the materials and methods for producing a range of small microcapsules containing selected cargo in a single step spray drying method of the present invention are depicted generally in FIG. 1 through FIG. 4. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Generally, the synthesis of alginate microcapsules and films is used to illustrate the technology. Although the methods are demonstrated in the context of alginate encapsulation, the apparatus and methods can be adapted and applied to the use of other polymer materials as well.

Figure 1:
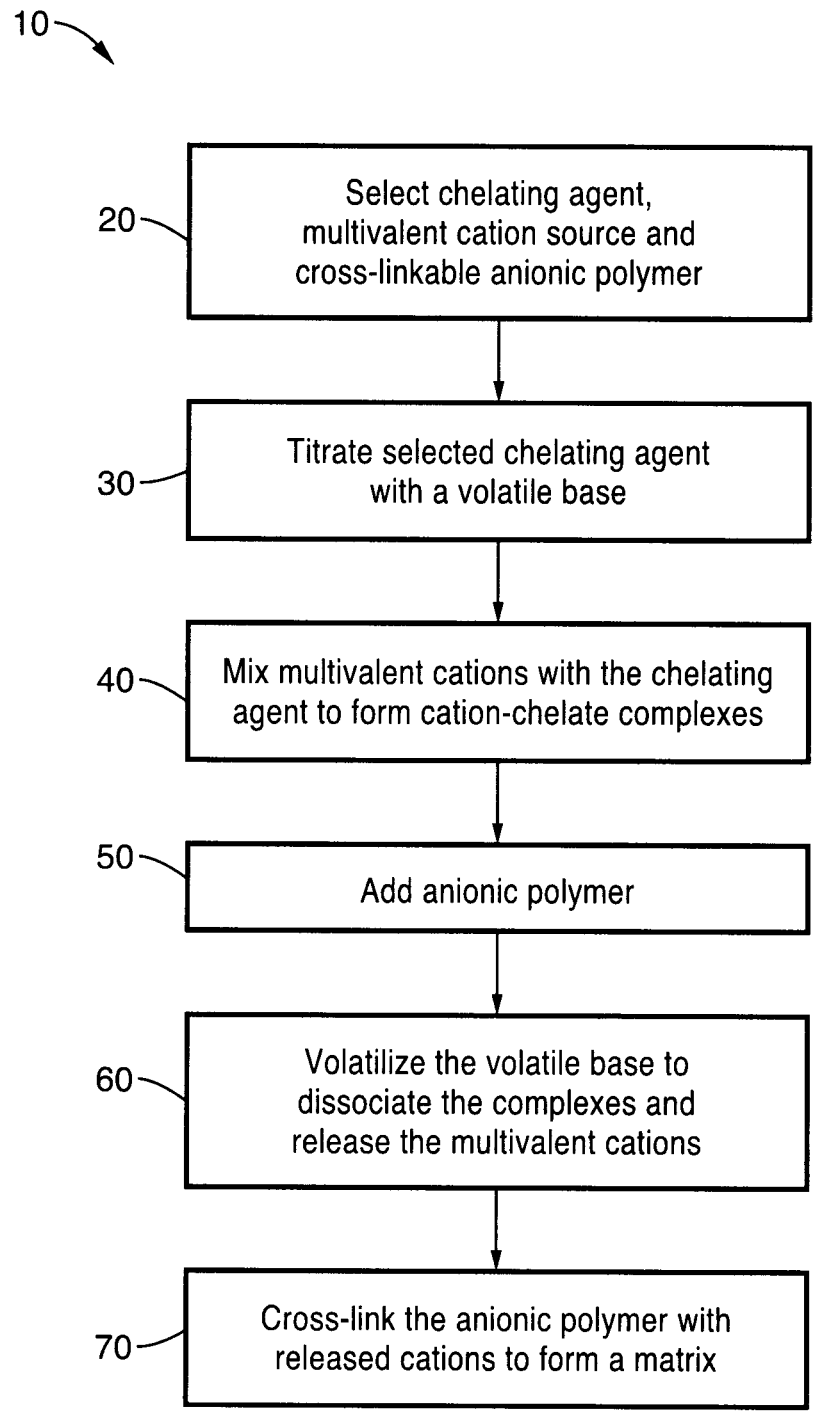
FIG. 1 is a functional block diagram of a method for fabricating microcapsules, fibers or films with a single polymerization step according to one embodiment of the technology.

Turning now to FIG. 1, a flow diagram of one embodiment of a method 10 for the formation of a polymerized polymer film or capsule is shown schematically. The first step at block 20 of FIG. 1 is the selection of at least one cross-linkable anionic polymer and a source of multivalent cations that will polymerize the polymer as well as a sequestering agent that may sequester the selected cations in solution.

Suitable polymers that can be used for encapsulation include alginates, soy or whey proteins, collagen, carboxymethylcellulose, hyaluronic acid, carrageenan, polygalacturonates (pectins) and other polymers that will spontaneously cross-link in the presence of multivalent cations. The formulation can also be a mixture of matrix polymer types including mixtures of polymers and proteins and copolymers. Formulations with mixed polymer types can improve the protection of the biological material that is being encapsulated.

The term polymer is used in the general sense to refer to the molecular entity or unit that has at least one functional cross-linkable moiety that physically or chemically cross-links in the presence of a multivalent ion and the terms are not intended to be limiting. The polymerized unit may be a high molecular weight polymer or may be oligomeric. Any molecule that cross-links with multivalent ions is a candidate polymer.

The source of multivalent cations or crosslinking agents are preferably water-soluble salts that initiate cross-linking including those that contain divalent ions such as $Ca^{2+}$, $Ba^{2+}$, and $Zn^{2+}$ or soluble trivalent salts such as aluminum chloride ($AlCl_3$) or chromium chloride $CrCl_3$). Particularly preferred sources of crosslinking cations for use with alginate, for example, include calcium chloride, magnesium chloride and ferrous chloride. Although chlorine-based salts are preferred, salts with non-chloride anions (e.g. calcium sulfate) are also suitable. Barium salts and other cations, such as Co, Cu, $Fe^{2+}$, etc., that have been explored in biomedical applications may also be used.

Cation sequestration is preferably accomplished with chelating agents that form a soluble cation-chelating agent complex. Calcium binding of chelating agents such as Maleic acid oligomer (MAO), Phytic acid, Citric acid and Nitrilotriacetic acid (NTA) are preferred with calcium sequestration for example. Other suitable chelating agents include thioglycolic acid, 2,3, dihydroxybenzoic acid, tripolyphosphate, polyacrylic acid, acrylic acid copolymers and maleic acid copolymers.

There are a large number of chelating agent candidates that can be used to sequester the multivalent cations. The pH responsiveness of the chelating agent is the key to either sequestering the multivalent ions or releasing them for crosslinking polymers and this characteristic is one factor in the selection of the chelating agent at block 20.

The sequestering agent that was selected at block 20 is titrated with a volatile base in block 30 to ready the chelating agent to accept cations in block 40 of FIG. 1. Preferred volatile bases include ammonium hydroxide and volatile amine compounds such as methylamine, trimethylamine, ethylamine, diethylamine and triethylamine. Other suitable volatile bases include isobutylamine, N,N-diisopropylethylamine, morpholine, piperazine, and ethylenediamine. While these volatile bases are preferred, it will be understood that many different types of volatile bases could be selected.

The selected source of multivalent cations is then mixed with the solution of the sequestering chelating agent and volatile base at block 40. The selected cation source is a multivalent cation salt that can form a soluble complex with the chelating agent immobilizing the cation. The chelating ligands typically form two or more separate coordinated bonds with the cation.

For example, a carboxylate anion or phosphate anion can coordinate with the multivalent cation in the formation of the chelate-cation complex. The presence of nitrogen, oxygen or sulfur atoms with lone electron pairs in the chelating agent can also participate in forming the chelate-cation complex through lone pair electron coordination with the multivalent cation. Mixed acids and ether functionality in one molecule such as oxydiacetate can also produce multivalent cation-chelator complexes.

The coordinating ability of the sequestering chelating agent is a function of pH. Since the majority of chelating sequestering agents have an acidic functionality, the pH of the chelate solution is acidic.

The chelate equilibrium constant (K) relates the concentrations of unassociated chelating agent, unassociated multivalent cation, and cation-chelate complex. If calcium (Ca) is the multivalent cation, then $$K = \frac{[CaA^{(n-2)^-}]}{[Ca^{2+}][A^{n-}]}$$

where A represents the chelating agent and n represents the magnitude of anionic charge on the chelator. The brackets signify concentration. Greater values of K (or log(K)) indicate a stronger affinity of the chelator to form a complex. The log(K) value for chelating agents is pH dependent, and the nature of the pH dependency is unique to each chelating agent.

Accordingly, the selection of the chelating agent at block 20 will include agents with the highest value of K at the upper pH value after the addition of the volatile base in order to minimize the presence of free cations in the final film or spray solution.

Figure 4:
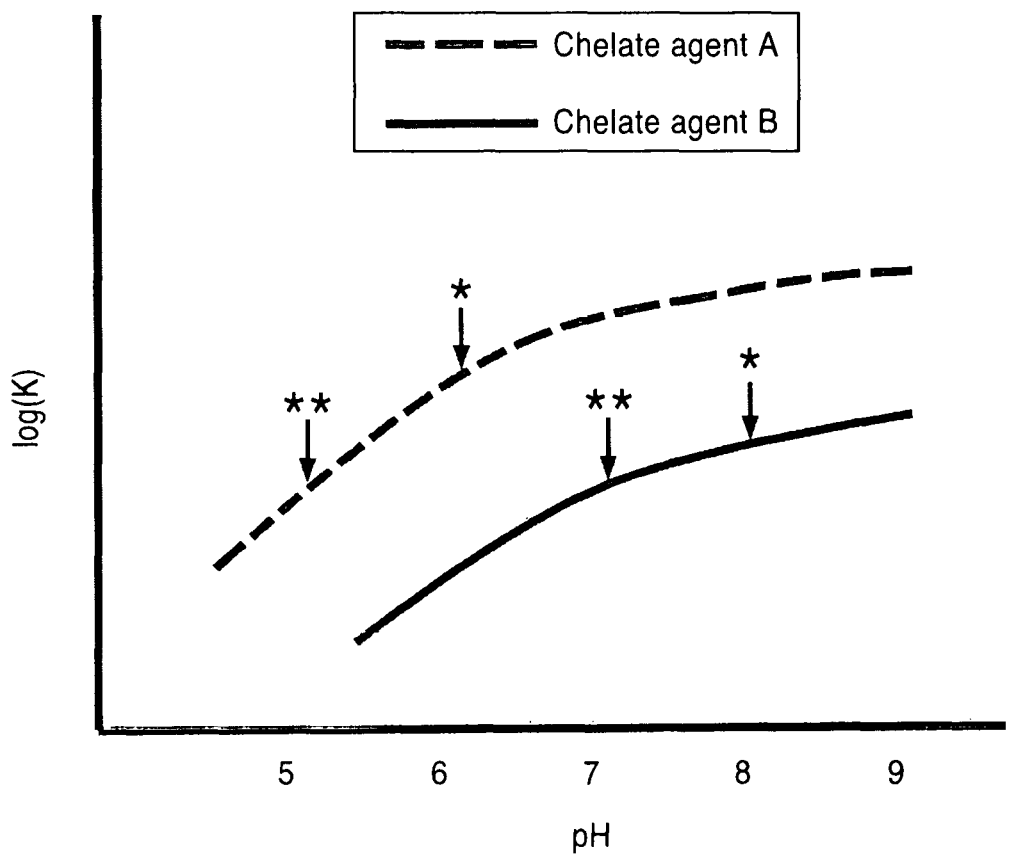
FIG. 4 is a graph of the relationship of log(K) to pH for two hypothetical chelating agents, where (*) represents the logK for a feed solution after addition of a volatile base and (**) represents the logK after the loss of the volatile base. K=Concentration of Ca++ Chelating agent complex divided by the product of the concentration of Ca++ and the concentration of free chelating agent.

FIG. 4 illustrates the relationship between log(K) and pH. FIG. 4 depicts a representation of the relationship of log(K) on pH for two hypothetical chelating agents. Single asterisk (*) indicates the log(K) for the feed solution after the addition of the volatile base. Double asterisk (**) indicates the log(K) during spray-drying after the loss of the volatile base during heating and drying. It can be seen from FIG. 4 that as the pH decreases, K decreases and the free cation ($Ca^{2+}$) concentration increases which are how available to facilitate cross-linking in the presence of the appropriate polymer. Table 1 summarizes several suitable chelating agents along with log(K) values at multiple pH levels.

The selected anionic polymer or polymers are added to the solution of cation-chelate complexes, volatile base and cargo for encapsulation to complete the formulation at block 50 of FIG. 1. The cross-linkable polymer that is added to this solution will remain freely dissolved until some disruption of equilibrium induces the release of the free multivalent cations from the cation-chelate complex.

Optionally, the solution formulation can also include a weak acid. The weak acid acts in combination with the acidic chelating agent to drop the pH after the volatile base has evaporated out. Suitable weak acids include Benzoic acid; Lactic acid; Ascorbic acid; Adipic acid; Acrylic acid; Glutaric acid; Ascorbic acid; Gallic acid; Caffeic acid; L-Tartaric acid; D-Tartaric acid; Malic acid; Succinic Acid; Fumaric acid and Maleic acid.

The formulated solution produced at block 50 of FIG. 1 can be deposited on a substrate to ultimately produce a film or coating or it can be placed in an atomizer or spray dryer to form capsules of variable sizes. The formulation can be applied to surfaces by printing, dip-coating or other application method or it can be used to form capsules, particles or fibers.

Film or capsule formation at block 60 of FIG. 1 is initiated by the volatilization of the volatile base of the formulation. As the coating or droplets dry, the volatile base in the formulation volatilizes, causing a drop in pH and the resulting protons outcompete the cation in the chelator-cation complex releasing multivalent cations. The released multivalent cations from the chelate-cation complex are now available to crosslink the polymers to form a film or capsule at block 70. Thus, cation-chelate complex dissociation provides the mechanism of cross-linking agent (multivalent cation) release to induce polymer cross-linking.

The methods may be further illustrated with an embodiment of the method 100 of FIG. 2 providing spray-drying of an aqueous formulation that contains an anionic carboxyl-containing polymer sodium alginate, a calcium chloride salt multivalent cation source, a phytic acid chelating agent and an ammonium hydroxide volatile base.

Referring now to FIG. 2, a spray formulation is prepared beginning with a solution of a phytic acid chelating agent, an ammonium hydroxide volatile base and cargo that are combined at block 110. The phytic acid chelating agent was selected because of the high K value at the upper pH value after the addition of ammonium hydroxide. During the formation of this solution, the acidic chelating agent is preferably titrated with the volatile ammonium hydroxide base to an elevated pH to improve the ion-binding capability of the chelating agent.

The cargo to be encapsulated should be stable at pH values in the range between the upper pH value after the addition of the volatile base and the lower pH value after volatilization of the volatile base. A wide variety of cargo can be selected and encapsulated for different uses at block 110 of FIG. 2. For example, the cargo can be organic or inorganic molecule compounds such as proteins, nucleotides, drugs, medicinal compositions, anti-bacterial agents or probiotics for animal, plant or human treatments. The cargo can also be individual cells, such as stem cells, for implantation. The cargo can also be selected for non-therapeutic uses such as aromatic compounds, oils, catalysts, initiators and other industrially relevant compounds.

At block 120 of FIG. 2, multivalent cations then are added and sequestered in cation-chelate complexes. In this illustration, the selected multivalent cation source, calcium chloride, is added to the initial solution of chelating agent and base. The calcium cations are completely chelated in solution by forming chelating agent-cation complexes.

The cross-linkable polymer, sodium alginate, is then added to the mix of chelating agent-cation complexes and cargo at block 130. The alginate will remain dissolved in solution until the multivalent cations that are immobilized in the cation-chelate complexes are released from the complex.

The solution in this fluid state is pumped through the nozzle of the spray dryer, where it is effectively atomized and heated at block 140. During spray drying (or other thermal treatment or thermal drying process) at block 140, ammonium from the volatile base decomposes into gaseous ammonia at block 150. As ammonia leaves the dehydrating droplet of solution, the pH of the solution drops since the chelating agents are generally acidic. As the pH decreases, the chelator becomes protonated, reducing its ability to bind multivalent cations. As a consequence, the cation-chelate complexes dissociate releasing the sequestered multivalent ions at block 150 of FIG. 2.

As the cation-chelate complexes dissociate, the liberated multivalent cations associate with the anionic polymer to form a cross-linked matrix to form a microcapsule at block 160. During spray-drying, the formation of a wet particle, polymer cross-linking, and particle drying occur nearly simultaneously.

Some of the functionalities of the components of the film forming or encapsulant compositions can be combined. For example, the polymer component of the composition that is selected can include the chelating agent functionality so the need for a separate chelating agent is eliminated. The starting composition in these embodiments is a polymeric chelating agent, a volatile base and a multivalent cation cross-linking agent. The methods utilize the same encapsulation mechanism with these alternative compositions as used with the compositions described in FIG. 1 and FIG. 2.

An alternative embodiment of the method 200 utilizing a composition with components with combined functionality is illustrated in FIG. 3. At block 210, a chelating polymer is selected such as polyacrylic acid shown in Table 1. The chelating polymer may also be a chelating agent bound to the polymer in one embodiment. The chelating polymer is combined with a volatile base and cargo is added at block 210 in this illustration. An appropriate multivalent cation crosslinking agent is then added at block 220 of FIG. 3. In another embodiment, the cargo is added with the cross-linking agent after the chelating polymer and volatile base combination is prepared or with the final combination.

The final encapsulant composition in this illustration is atomized and the droplets heated at block 230. The volatile base of the droplets is vaporized during the heating process at block 240 resulting in the release of multivalent cations from the chelating polymer. The availability of free cations allows cross-linking of the polymer by the cross-linking agent to produce a capsule around the cargo at block 250 or produce a film or fibers in other settings.

It can be seen that the methods provide a number of variables and element selections that allow them to be adapted to a variety of encapsulation or coating applications and control over capsule characteristics. For example, the degree of cross-linking and associated release rate of the encapsulated active ingredient cargo can be controlled by the choice of chelating agent, volatile base, polymer, ratio of multivalent cation to chelating agent and encapsulation conditions.

Control over the inlet temperature of spray dry air and other process conditions, for example, can provide control over the decomposition rate of the ammonium salt of the chelating agent and the liberation of ammonia, which is increased as inlet temperature is increased. The concentration of multivalent cation that is released from cation-chelate complexes and available for crosslinking can be controlled by the selected concentration of soluble metal cation salt relative to the concentration of chelating agent in the formulation. Optionally, a weak acid can be added for additional control over pH.

It can also be seen that the encapsulation mechanism described herein can be adapted to a variety of different component materials and formation condition manipulations. Although the technology is described with volatile bases and acidic chelating agents etc., the methods can also be adapted to use volatile acids and basic chelating agents etc.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the operational principles of the microcapsule production methods, a formulation of a cross-linkable anionic polymer (alginate featuring carboxyl groups), multivalent cation salt (calcium chloride), a chelating agent (phytic acid), and ammonium hydroxide (volatile base) were produced for spray drying. Microcapsules were produced and processed using the processing steps shown generally in FIG. 2.

The demonstration was conducted using a laboratory spray-dryer (Buchi B-290) with a feed solution of 0.375% phytic acid, 0.075% calcium chloride and 2% sodium alginate. During the formation of the feed solution, the phytic acidic chelating agent was titrated with ammonium hydroxide to an elevated pH of pH 6.1 to improve ion-binding capability.

The feed solution was pumped into a spray dryer to form droplets and capsules under the following spray dryer conditions: $T_{inlet}$=150° C., $T_{outlet}$=65° C., Pump=30%, Air flow pressure head=40 mm and the Aspirator=100%. This resulted in a powder product.

A 1% suspension of the resulting powder in water (pH of suspension was 5.89) remained partially insoluble: 62.5% of alginate in the powder dissolved, while 37.5% of alginate remained insoluble in the particles.

Example 2

To better understand the microcapsule production methods, a formulation with different concentrations of multivalent cation salt (calcium chloride) and the chelating agent (phytic acid) were used for comparison and to demonstrate control over some capsule characteristics.

In this demonstration, an aqueous feed solution of sodium alginate polymer was mixed with a phytic acid chelating agent, a calcium chloride source of multivalent cations and ammonium hydroxide to a pH that was sufficiently high so that the calcium ions were completely chelated in solution. A laboratory spray-dryer (Buchi B-290) was loaded with a feed solution of 1.13% phytic acid, 0.225% calcium chloride and 2% sodium alginate that was adjusted to pH 6.19 with ammonium hydroxide.

The feed solution was atomized into an evaporation chamber of the spray dryer to form droplets and capsules under the following spray dryer conditions: $T_{inlet}$=180° C., $T_{outlet}$=99° C., Pump=20% and Air flow pressure head=40 mm, Aspirator=100%.

As the droplets dried, ammonium hydroxide in the formulation volatilized, causing a drop in pH allowing protons to outcompete the Ca ion in the cation-chelator complex. The resulting release of Ca ions into the droplet solution crosslinked the alginates to form a matrix. Particles collected at the outlet of the evaporation chamber of the dryer were dried, cross-linked alginate microcapsules. A 1% suspension of the resulting powder in water (pH of suspension was 5.58) remained mostly insoluble: 25.6% of alginate in the powder dissolved, while 74.4% of alginate remained insoluble. However, based on the contents of Table 1, the greatest decrease in the log(K) of phytic acid occurs between pH 8.4 and 7.1; therefore, increasing the pH of the inlet solution to 8.4 should allow for the release of a greater quantity of calcium cations and thus enhance cross-linking.

Example 3

The inclusion of a hydrophilic cargo in the microcapsules was demonstrated by formulating with hyaluronic acid as the cargo, calcium chloride as the multivalent cation salt, phytic acid as the chelating agent and sodium alginate as the matrix polymer.

A laboratory spray-dryer (Buchi B-290) was loaded with a feed solution of 0.3125% phytic acid, 0.0625% calcium chloride, 1.37% Hyaluronic Acid and 0.5% sodium alginate that was adjusted to pH 8.4 with ammonium hydroxide.

The feed solution was atomized into an evaporation chamber of the spray dryer to form droplets and hyaluronic acid containing capsules under the following spray dryer conditions: $T_{inlet}$=180° C., Pump=20% and Air flow pressure head=40 mm, Aspirator=100%.

The resulting powder, containing 50% (d.b.) hyaluronic acid was suspended in water to confirm crosslinking of the alginates in the microcapsules. After 2 hours of agitation in water, the pH of the suspension was pH 6.3, with 75.77±4.9% of the alginates in the microcapsules remaining insoluble (i.e. an extent of crosslinking in the microcapsules of 76%). A control sample formulated and formed similarly but without the hyaluronic acid cargo had an extent of crosslinking of 81.9±4.5%. Unreleased hyaluronic acid loaded microcapsules exhibited a 11.48× (or 1148%) reduction in Water Absorption Capacity (by weight) compared to cross-linked unloaded microcapsules. Unreleased hyaluronic acid loaded microcapsules displayed 0.5104× (51.04%) lower volume growth compared to cross-linked unloaded microcapsules. These samples demonstrate successful formation of hydrophilic cargo loaded cross-linked alginate microcapsules formed by controlling the timing of the calcium ion availability with an acidic chelating agent and volatile base during spray drying. The addition of hydrophilic cargo that is in addition an anionic polymer reduces microcapsule water uptake showing cargo participation in cross-linking with multi-valent cations.

Example 4

A formulation with fixed concentrations of multivalent cation salt (calcium chloride) and the chelating agent (citric acid) were used to demonstrate the ability to form cross-linked unloaded and loaded microcapsules by varied acidic chelators with different K values. Sodium alginate was the matrix polymer and loaded microcapsules contained hydrophilic cargo (hyaluronic acid). An additional acid was included in this formulation to further reduce the final pH of the matrix to facilitate cross-linking.

A formulation of 0.5% sodium alginate, 0.125% calcium chloride, 0.75% citric acid, and 0.375% succinic acid was adjusted to pH 7 with ammonium hydroxide. The feed solution was atomized into an evaporation chamber of the spray dryer to form droplets at the following spray dryer conditions: $T_{inlet}$=170° C., Pump=20% and Air flow pressure head=40 mm, Aspirator=100%. A 1% suspension of the resulting powder in water (pH of suspension was 5.178) remained partially insoluble after 30 min of agitation.

The addition of an acid that does not complex with the multivalent cation to form an insoluble salt allows for the volatilization of base to bring the pH of the feed solution below the pKa of a weak acid chelator with limited carboxylic acid availability.

From the description herein, it will be appreciated that the present disclosure encompasses multiple embodiments which include, but are not limited to, the following:

1. A method of cross-linking polymer molecules, the method comprising: (a) providing a solution of an acidic chelating agent with a volatile base; (b) adding at least one source of multivalent cations to form cation-chelate complexes in the solution; (c) mixing molecules of at least one anionic polymer with the solution of cation-chelate complexes and volatile base; and (d) vaporizing the volatile base of the solution, thereby disassociating the cation-chelate complexes and releasing multivalent cations and cross-linking the polymer molecules with the multivalent cations.

2. The method of any preceding or following embodiment, said acidic chelating agent solution further comprising a weak acid.

3. The method of any preceding or following embodiment, wherein the weak acid is an acid selected from the group consisting of benzoic acid, lactic acid, ascorbic acid, adipic acid, acrylic acid, glutaric acid, ascorbic acid, gallic acid, caffeic acid, L-Tartaric acid, D-Tartaric acid, malic acid, succinic acid, fumaric acid and maleic acid.

4. The method of any preceding or following embodiment, wherein the chelating agent is selected from the group of chelating agents consisting of maleic acid oligomer (MAO), Phytic acid, Citric acid, hyaluronic acid and Nitrilotriacetic acid (NTA).

5. The method of any preceding or following embodiment, wherein the chelating agent is selected from the group of chelating agents consisting of thioglycolic acid, 2,3, dihydroxybenzoic acid, tripolyphosphate, polyacrylic acid, acrylic acid copolymers and maleic acid copolymers.

6. The method of any preceding or following embodiment, wherein the volatile base is ammonium hydroxide.

7. The method of any preceding or following embodiment, wherein the volatile base is selected from the group of volatile amine bases consisting of methylamine, trimethylamine, ethylamine, diethylamine and triethylamine, isobutylamine, N,N-diisopropylethylamine, morpholine, piperazine, and ethylenediamine.

8. The method of any preceding or following embodiment, wherein the source of multivalent cations is a metal salt selected from the group of multivalent metal salts consisting of calcium chloride, magnesium chloride and ferric chloride.

9. The method of any preceding or following embodiment, wherein the source of multivalent cations is a trivalent metal salt selected from the group of metal salts consisting of aluminum chloride ($AlCl_3$), chromium chloride ($CrCl_3$) or ferric chloride ($FeCl_3$).

10. The method of any preceding or following embodiment, wherein the polymer is selected from the group of polymers consisting of alginates, carboxymethylcellulose, carrageenan, hyaluronic acid, polygalacturonates, collagen, soy proteins and whey proteins.

11. The method of any preceding or following embodiment, further comprising: controlling volatile base vaporization temperatures to control rate of disassociation of cation-chelate complexes and release of multivalent cations.

12. The method of any preceding or following embodiment, further comprising: controlling a degree of polymer cross-linking with chelating agent concentration and multivalent ion concentration.

13. A method for producing microcapsules, the method comprising: (a) providing a solution comprising: (i) polymer molecules; (ii) a volatile base; (iii) multivalent cation-chelate complexes; and (iv) cargo; (b) atomizing the solution to form droplets; and (c) volatilizing the volatile base of the droplets, thereby lowering a pH of the solution and disassociating the multivalent cation-chelate complexes releasing multivalent cations that cross-link the polymer molecules to form a microcapsule around the cargo.

14. The method of any preceding or following embodiment, wherein the solution further comprises a weak acid selected from the group consisting of benzoic acid, lactic acid, ascorbic acid, adipic acid, acrylic acid, glutaric acid, ascorbic acid, gallic acid, caffeic acid, L-Tartaric acid, D-Tartaric acid, malic acid, fumaric acid, succinic acid and maleic acid.

15. The method of any preceding or following embodiment, wherein the chelating agent is selected from the group of chelating agents consisting of maleic acid oligomer (MAO), Phytic acid, Citric acid, hyaluronic acid and Nitrilotriacetic acid (NTA).

16. The method of any preceding or following embodiment, wherein the chelating agent is selected from the group of chelating agents consisting of thioglycolic acid, 2,3, dihydroxybenzoic acid, tripolyphosphate, polyacrylic acid, acrylic acid copolymers and maleic acid copolymers.

17. The method of any preceding or following embodiment, wherein the volatile base is ammonium hydroxide.

18. The method of any preceding or following embodiment, wherein the volatile base is selected from the group of volatile amine bases consisting of methylamine, trimethylamine, ethylamine, diethylamine and triethylamine, isobutylamine, N,N-diisopropylethylamine, morpholine, piperazine, and ethylenediamine.

19. The method of any preceding or following embodiment, wherein the source of multivalent cations is a metal salt selected from the group of divalent metal salts consisting of calcium chloride and magnesium chloride.

20. The method of any preceding or following embodiment, wherein the source of multivalent cations is a trivalent metal salt selected from the group of metal salts consisting of aluminum chloride ($AlCl_3$), chromium chloride ($CrCl_3$) or ferric chloride ($FeCl_3$).

21. The method of any preceding or following embodiment, wherein the polymer is selected from the group of polymers consisting of alginates, carboxymethylcellulose, carrageenan, hyaluronic acid, polygalacturonates, collagen, soy proteins and whey proteins.

22. The method of any preceding or following embodiment, further comprising: controlling volatile base vaporization temperatures to control rate of disassociation of cation-chelate complexes and release of multivalent cations.

23. The method of any preceding or following embodiment, further comprising: controlling a degree of polymer cross-linking with chelating agent concentration and multivalent ion concentration.

24. An encapsulant or film forming composition, comprising: (a) molecules of at least one polymer; (b) a volatile base; (c) a source of multivalent cations; and (d) a chelating agent; (e) wherein the multivalent cations and chelating agents form multivalent cation-chelate complexes.

25. The composition of any preceding or following embodiment, further comprising a weak acid.

26. The composition of any preceding or following embodiment, wherein the weak acid is selected from the group consisting of benzoic acid, lactic acid, ascorbic acid, adipic acid, acrylic acid, glutaric acid, ascorbic acid, gallic acid, caffeic acid, L-Tartaric acid, D-Tartaric acid, malic acid, fumaric acid and maleic acid.

27. The composition of any preceding or following embodiment, wherein the polymer is selected from the group of polymers consisting of alginates, carboxymethylcellulose, carrageenan, hyaluronic acid, polygalacturonates, collagen, soy proteins and whey proteins.

28. The composition of any preceding or following embodiment, wherein the volatile base is selected from the group of volatile amine bases consisting of methylamine, trimethylamine, ethylamine, diethylamine and triethylamine, isobutylamine, N,N-diisopropylethylamine, morpholine, piperazine, and ethylenediamine.

29. The composition of any preceding or following embodiment, wherein the volatile base is ammonium hydroxide.

30. The composition of any preceding or following embodiment, wherein the source of multivalent cations is a metal salt selected from the group of divalent metal salts consisting of calcium chloride and magnesium chloride.

31. The composition of any preceding or following embodiment, wherein the source of multivalent cations is a trivalent metal salt selected from the group of metal salts consisting of aluminum chloride ($AlCl_3$), chromium chloride ($CrCl_3$) or ferric chloride ($FeCl_3$).

32. The composition of any preceding or following embodiment, wherein the chelating agent is selected from the group of chelating agents consisting of maleic acid oligomer (MAO), Phytic acid, Citric acid, hyaluronic acid and Nitrilotriacetic acid (NTA).

33. The composition of any preceding or following embodiment, wherein the chelating agent is selected from the group of chelating agents consisting of thioglycolic acid, 2,3, dihydroxybenzoic acid, tripolyphosphate, polyacrylic acid, acrylic acid copolymers and maleic acid copolymers.

34. An encapsulant or film forming composition, comprising: (a) molecules of at least one polymeric chelating agent; (b) a volatile base; (c) a source of multivalent cations; and (d) wherein the multivalent cations and polymeric chelating agents form multivalent cation-chelate polymer complexes.

35. The composition of any preceding or following embodiment, wherein the polymeric chelating agent is polyacrylic acid.

36. The composition of any preceding or following embodiment, wherein the volatile base is selected from the group of volatile amine bases consisting of methylamine, trimethylamine, ethylamine, diethylamine and triethylamine, isobutylamine, N,N-diisopropylethylamine, morpholine, piperazine, and ethylenediamine.

37. The composition of any preceding or following embodiment, wherein the volatile base is ammonium hydroxide.

38. The composition of any preceding or following embodiment, wherein the source of multivalent cations is a metal salt selected from the group of divalent metal salts consisting of calcium chloride and magnesium chloride.

39. The composition of any preceding or following embodiment, wherein the source of multivalent cations is a trivalent metal salt selected from the group of metal salts consisting of aluminum chloride ($AlCl_3$), chromium chloride ($CrCl_3$) or ferric chloride ($FeCl_3$).

40. The composition of any preceding or following embodiment, further comprising a weak acid.

41. The composition of any preceding or following embodiment, wherein the weak acid is an acid selected from the group consisting of benzoic acid, lactic acid, ascorbic acid, adipic acid, acrylic acid, glutaric acid, ascorbic acid, gallic acid, caffeic acid, L-Tartaric acid, D-Tartaric acid, malic acid, succinic acid, fumaric acid and maleic acid.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Calcium Binding of Chelating Agents

| Chelating Agent | Potential initial condition pH & log(K) | Potential final condition pH & log(K) |
| --- | --- | --- |
| Maleic acid oligomer (MAO) | log(K) = 3.7 at pH 9.7 | log(K) = 2.66 at pH 6.5 |
| Citric acid | log(K) = 4.1 at pH 9.7 | Log(K) = 3.7 at pH 6.8 |
| Nitrilotriacetic acid (NTA) | log(K) = 6.1 at pH 9.7 | Log(K) = 5.1 at pH 7.95 |
| Phytic acid | The largest drop in log(K) occurs between pH 8.4 and 7.2 | |
| Polyacrylic acid | The largest drop in log(K) occurs between pH 7 and pH 4.6 | |

What is claimed is:

1. A method of cross-linking polymer molecules, the method comprising:
   (a) providing a solution of an acidic chelating agent with a volatile base;
   (b) adding at least one source of multivalent cations to form cation-chelate complexes in the solution;
   (c) mixing molecules of at least one anionic polymer with the solution of cation-chelate complexes and volatile base; and
   (d) vaporizing the volatile base of the solution, thereby disassociating the cation-chelate complexes and releasing multivalent cations and cross-linking the polymer molecules with said multivalent cations.

2. The method of claim 1, said acidic chelating agent solution further comprising a weak acid buffer.

3. The method of claim 2, wherein said weak acid is an acid selected from the group consisting of benzoic acid, lactic acid, ascorbic acid, adipic acid, acrylic acid, glutaric acid, ascorbic acid, gallic acid, caffeic acid, L-Tartaric acid, D-Tartaric acid, malic acid, fumaric acid and maleic acid.

4. The method of claim 1, wherein said chelating agent is selected from the group of chelating agents consisting of maleic acid oligomer (MAO), Phytic acid, Citric acid, hyaluronic acid and Nitrilotriacetic acid (NTA).

5. The method of claim 1, wherein said chelating agent is selected from the group of chelating agents consisting of thioglycolic acid, 2,3, dihydroxybenzoic acid, tripolyphosphate, polyacrylic acid, acrylic acid copolymers and maleic acid copolymers.

6. The method of claim 1, wherein said volatile base is ammonium hydroxide.

7. The method of claim 1, wherein said volatile base is selected from the group of volatile amine bases consisting of methylamine, trimethylamine, ethylamine, diethylamine and triethylamine, isobutylamine, N, N-diisopropylethylamine, morpholine, piperazine, and ethylenediamine.

8. The method of claim 1, wherein said source of multivalent cations is a metal salt selected from the group of multivalent metal salts consisting of calcium chloride, magnesium chloride and ferric chloride.

9. The method of claim 1, wherein said source of multivalent cations is a trivalent metal salt selected from the group of metal salts consisting of aluminum chloride ($AlCl_3$), chromium chloride ($CrCl_3$) or ferric chloride ($FeCl_3$).

10. The method of claim 1, wherein said polymer is selected from the group of polymers consisting of alginates, carboxymethylcellulose, carrageenan, hyaluronic acid, polygalacturonates, collagen, soy proteins and whey proteins.

11. The method of claim 1, further comprising controlling volatile base vaporization temperatures to control rate of disassociation of cation-chelate complexes and release of multivalent cations.

12. The method of claim 1, further comprising controlling a degree of polymer cross-linking with chelating agent concentration and multivalent ion concentration.

* * * * *